(12) United States Patent
Kim et al.

(10) Patent No.: US 10,761,047 B2
(45) Date of Patent: Sep. 1, 2020

(54) FORMALDEHYDE DETECTING APPARATUS, AND AIR TREATMENT APPARATUS HAVING THE SAME

(71) Applicant: Samsung Electronics Co., Ltd., Suwon-si (KR)

(72) Inventors: Tae-gyu Kim, Hwaseong-si (KR); Jae-ho Baek, Seoul (KR); Jong-soo Hong, Yongin-si (KR); Si-hoon Lee, Yongin-si (KR); Jeong-su Han, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 99 days.

(21) Appl. No.: 15/653,797

(22) Filed: Jul. 19, 2017

(65) Prior Publication Data

US 2018/0024090 A1    Jan. 25, 2018

(30) Foreign Application Priority Data

Jul. 25, 2016  (KR) .......................... 10-2016-0094174

(51) Int. Cl.
*G01N 33/00* (2006.01)
*G01N 27/404* (2006.01)
(Continued)

(52) U.S. Cl.
CPC .......... *G01N 27/4045* (2013.01); *F24F 11/30* (2018.01); *G01N 1/2273* (2013.01);
(Continued)

(58) Field of Classification Search
CPC ................................................. G01N 33/0009
See application file for complete search history.

(56) References Cited

U.S. PATENT DOCUMENTS

| | | |
|---|---|---|
| 5,337,605 A | 8/1994 | Schultz et al. |
| 2005/0257540 A1 | 11/2005 | Choi et al. |

(Continued)

FOREIGN PATENT DOCUMENTS

| | | |
|---|---|---|
| CN | 202421111 | 9/2012 |
| CN | 203502053 | 3/2014 |

(Continued)

OTHER PUBLICATIONS

Extended European Search Report dated Sep. 28, 2017 in European Patent Application No. 17182086.3.

(Continued)

*Primary Examiner* — Lisa M Caputo
*Assistant Examiner* — Alex T Devito
(74) *Attorney, Agent, or Firm* — Staas & Halsey LLP

(57) ABSTRACT

A formaldehyde detecting apparatus includes a formaldehyde sensor configured to measure concentration of formaldehyde in air; a printed circuit board on which the formaldehyde sensor is disposed, the printed circuit board including a signal processor configured to process a signal output from the formaldehyde sensor; a fixing member disposed on the printed circuit board, the fixing member configured to fix the formaldehyde sensor, wherein the fixing member prevents the formaldehyde sensor from oscillating with respect to the printed circuit board by external vibration; and a power supply configured to supply a voltage capable of stabilizing an output signal to the signal processor.

18 Claims, 17 Drawing Sheets

(51) Int. Cl.
  *F24F 11/30*  (2018.01)
  *G01N 1/22*  (2006.01)
  *G01N 27/416*  (2006.01)
  *F24F 110/50*  (2018.01)
(52) U.S. Cl.
  CPC ..... *G01N 27/4163* (2013.01); *G01N 33/0006* (2013.01); *G01N 33/0009* (2013.01); *G01N 33/0047* (2013.01); *F24F 2110/50* (2018.01)

(56) References Cited

U.S. PATENT DOCUMENTS

| | | | | |
|---|---|---|---|---|
| 2006/0288759 | A1* | 12/2006 | Okumura | G01N 27/4062 73/31.05 |
| 2014/0058690 | A1* | 2/2014 | Tian | G01D 21/02 702/62 |

FOREIGN PATENT DOCUMENTS

| | | |
|---|---|---|
| CN | 104181318 | 12/2014 |
| CN | 204730876 | 10/2015 |
| KR | 10-2005-0111154 | 11/2005 |
| KR | 10-2007-0058901 | 6/2007 |
| KR | 10-2013-0095336 | 8/2013 |
| KR | 10-2015-0070787 | 6/2015 |
| KR | 10-2016-0019577 | 2/2016 |

OTHER PUBLICATIONS

European Communication dated Sep. 24, 2018 in European Patent Application No. 17182086.3.
European Communication dated Jul. 17, 2019 in European Patent Application No. 17182086.3.

* cited by examiner

FORMALDEHYDE DETECTING APPARATUS, AND AIR TREATMENT APPARATUS HAVING THE SAME

CROSS-REFERENCE TO RELATED APPLICATIONS

This application claims priority from Korean Patent Application No. 10-2016-0094174 filed Jul. 25, 2016 in the Korean Intellectual Property Office, the disclosure of which is incorporated herein by reference in its entirety.

BACKGROUND

1. Field

The present disclosure relates to a formaldehyde detecting apparatus that can measure the concentration of formaldehyde in air. More particularly, the present disclosure relates to a formaldehyde detecting apparatus that can output a signal with stability and linearity, and an air treatment apparatus having the same.

2. Description of the Related Art

Building materials and interior materials including chemical materials are widely used for modern structures such as houses and buildings. However, these building materials and interior materials release various chemical substances into the air and contaminate the air in the room, thereby adversely affecting the health of people living in the room.

Presently, formaldehyde contained in building materials, interior materials and the like is known as a main material that pollutes the air. Therefore, a variety of measuring methods and measuring devices capable of measuring the concentration of formaldehyde in air have been developed and used.

In particular, air purifiers, air conditioners with an air purifying function and the like may include a formaldehyde sensor capable of detecting the concentration of formaldehyde contained in the air. A conventional formaldehyde sensor is configured to measure the concentration of formaldehyde in air by index and compare the measured index value with a reference value. Thus, when the measured formaldehyde index value is greater than the reference value, the user is informed that the formaldehyde concentration is higher than the reference value by sound or color. The user can then remove the formaldehyde in the air by ventilating the air in the room or by operating an air purifier or an air conditioner.

However, the conventional formaldehyde sensor nonlinearly outputs the signal related to the sensing concentration of the formaldehyde due to vibration generated when the air purifier or the air conditioner operates and/or unevenness of the supply voltage. In this way, when the output signal is nonlinear, the measured concentration of formaldehyde is inaccurate so that it is difficult to accurately identify the level of contamination of the air at present.

In addition, when the output of the formaldehyde sensor is nonlinear, it is impossible to accurately inform the user of the concentration of formaldehyde using numerals.

SUMMARY

The present disclosure has been developed in order to overcome the above drawbacks and other problems associated with the conventional arrangement. An aspect of the present disclosure relates to a formaldehyde detecting apparatus that can stabilize an output signal and maintain linearity by minimizing external vibration and noise generated by a supply voltage and an air treatment apparatus with the same.

According to an aspect of the present disclosure, a formaldehyde detecting apparatus may include a formaldehyde sensor configured to measure concentration of formaldehyde in air; a printed circuit board on which the formaldehyde sensor is disposed, the printed circuit board including a signal processor configured to process a signal output from the formaldehyde sensor; a fixing member disposed on the printed circuit board, the fixing member configured to fix the formaldehyde sensor, wherein the fixing member prevents the formaldehyde sensor from oscillating with respect to the printed circuit board by external vibration; and a power supply configured to supply a voltage capable of stabilizing an output signal to the signal processor.

The fixing member may include a base portion configured to fix and support the formaldehyde sensor; and a fastening portion vertically extending from the base portion, the fastening portion configured to fix the base portion to the printed circuit board.

The base portion of the fixing member may include a housing into which the formaldehyde sensor is inserted.

The fastening portion may include a pair of hooks, and the printed circuit board may be provided with a pair of fastening holes into which the pair of hooks is inserted.

The fixing member may include a support portion provided on a lower surface of the base portion, and the base portion may be located at a predetermined height on the printed circuit board and is kept parallel to the printed circuit board by the support portion.

The formaldehyde sensor may be fixed to an upper surface of the base portion with an adhesive or a double-sided tape.

The power supply may include a regulator that lowers a voltage of a supplied power, removes noise of the supplied power, and output a stabilized voltage.

The formaldehyde detecting apparatus may include an analog-to-digital converter electrically connected to the signal processor and configured to convert the signal output from the signal processor into a digital signal.

According to another aspect of the present disclosure, an air treatment apparatus may include a formaldehyde detecting apparatus provided with a formaldehyde sensor capable of measuring concentration of formaldehyde in air; and an air suction apparatus. The formaldehyde detecting apparatus may include a printed circuit board on which the formaldehyde sensor is disposed, the printed circuit board including a signal processor configured to process a signal output from the formaldehyde sensor; a fixing member disposed on the printed circuit board, the fixing member configured to fix the formaldehyde sensor, wherein the fixing member prevents the formaldehyde sensor from oscillating with respect to the printed circuit board by external vibration; and a power supply provided in the printed circuit board, the power supply configured to supply a stabilized voltage to the signal processor.

The air treatment apparatus may include a number display configured to display the digital signal output from the analog-to-digital converter by numerals. The number display may be configured to display a number below a decimal point.

The air treatment apparatus may include an identifying portion configured to compare the digital signal output from the analog-to-digital converter with a reference value of a formaldehyde concentration; and an audio output portion configured to output a comparing result of the identifying portion by sound.

The air treatment apparatus may include an adjusting portion configured to adjust the digital signal output from the analog-to-digital converter.

Other objects, advantages and salient features of the present disclosure will become apparent from the following detailed description, which, taken in conjunction with the annexed drawings, discloses preferred embodiments.

BRIEF DESCRIPTION OF THE DRAWINGS

These and/or other aspects and advantages of the present disclosure will become apparent and more readily appreciated from the following description of the embodiments, taken in conjunction with the accompanying drawings of which.

Throughout the drawings, like reference numerals will be understood to refer to like parts, components and structures.

DETAILED DESCRIPTION OF THE EXEMPLARY EMBODIMENTS

Hereinafter, certain exemplary embodiments of the present disclosure will be described in detail with reference to the accompanying drawings.

The matters defined herein, such as a detailed construction and elements thereof, are provided to assist in a comprehensive understanding of this description. Thus, it is apparent that exemplary embodiments may be carried out without those defined matters. Also, well-known functions or constructions are omitted to provide a clear and concise description of exemplary embodiments. Further, dimensions of various elements in the accompanying drawings may be arbitrarily increased or decreased for assisting in a comprehensive understanding.

The terms used in the present application are only used to describe the exemplary embodiments, but are not intended to limit the scope of the disclosure. The singular expression also includes the plural meaning as long as it does not differently mean in the context. In the present application, the terms "include" and "consist of" designate the presence of features, numbers, steps, operations, components, elements, or a combination thereof that are written in the specification, but do not exclude the presence or possibility of addition of one or more other features, numbers, steps, operations, components, elements, or a combination thereof.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
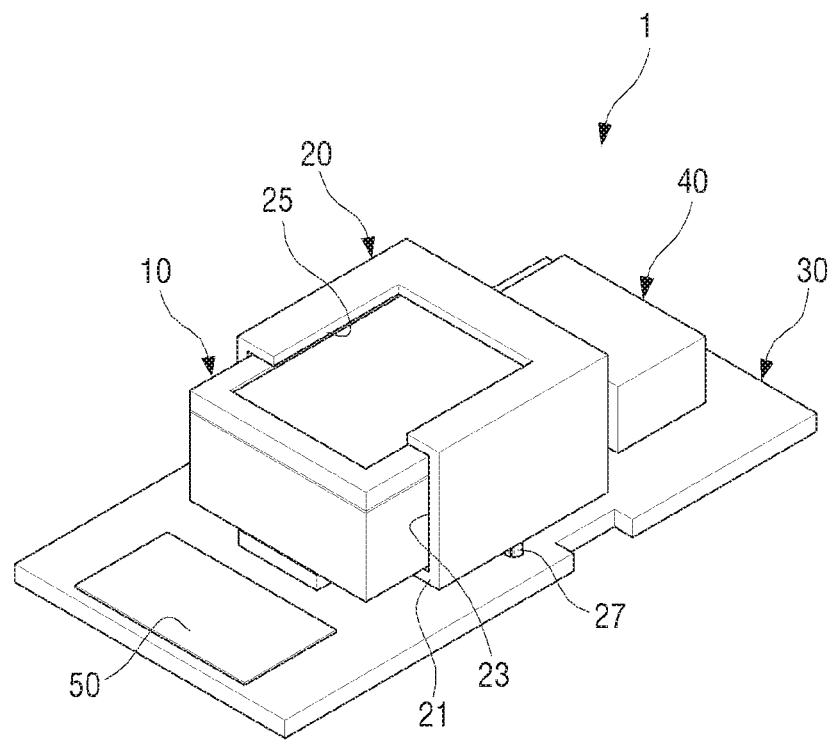
FIG. 1 is a perspective view illustrating a formaldehyde detecting apparatus according to an embodiment of the present disclosure.
Figure 2:
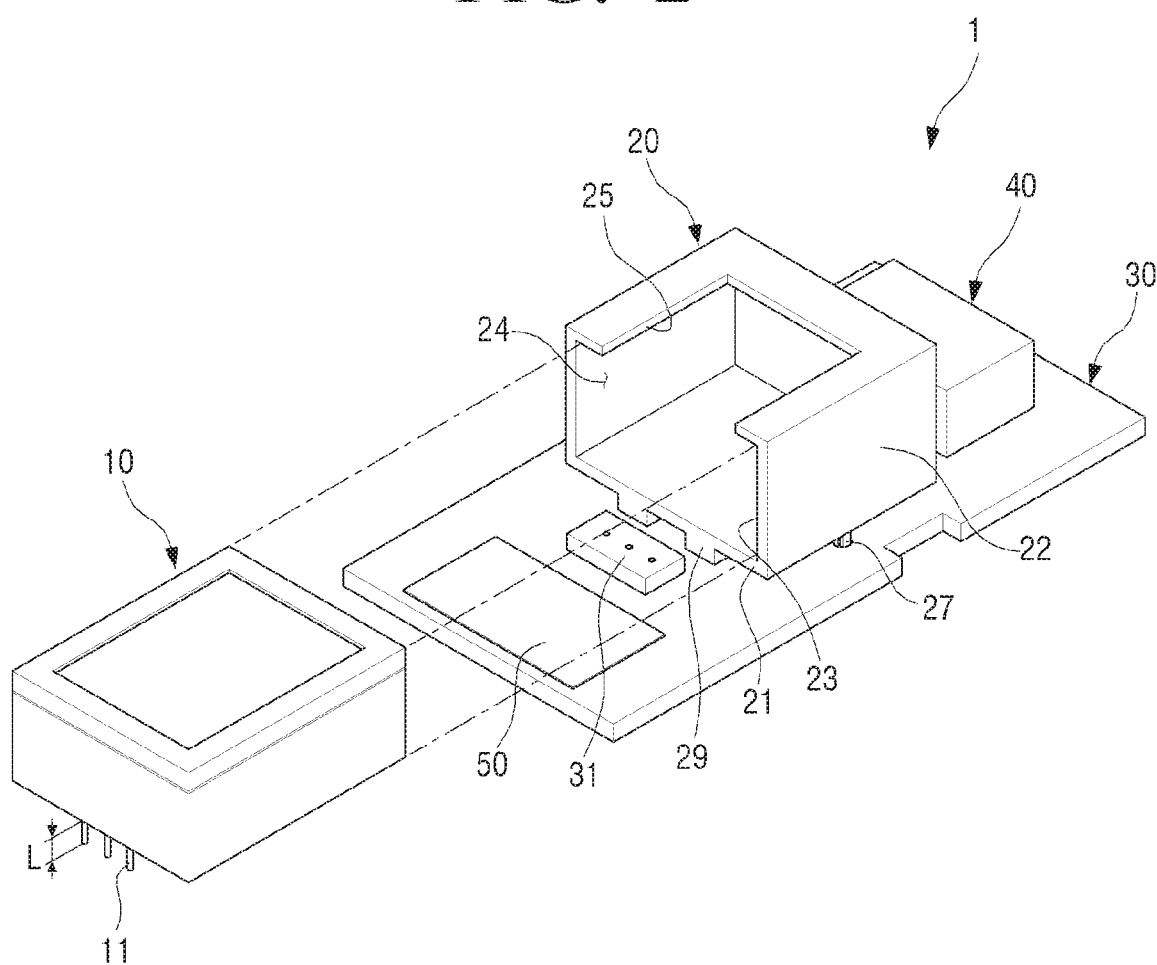
FIG. 2 is a perspective view illustrating a state in which a formaldehyde sensor is separated from the formaldehyde detecting apparatus of FIG. 1.
Figure 3:
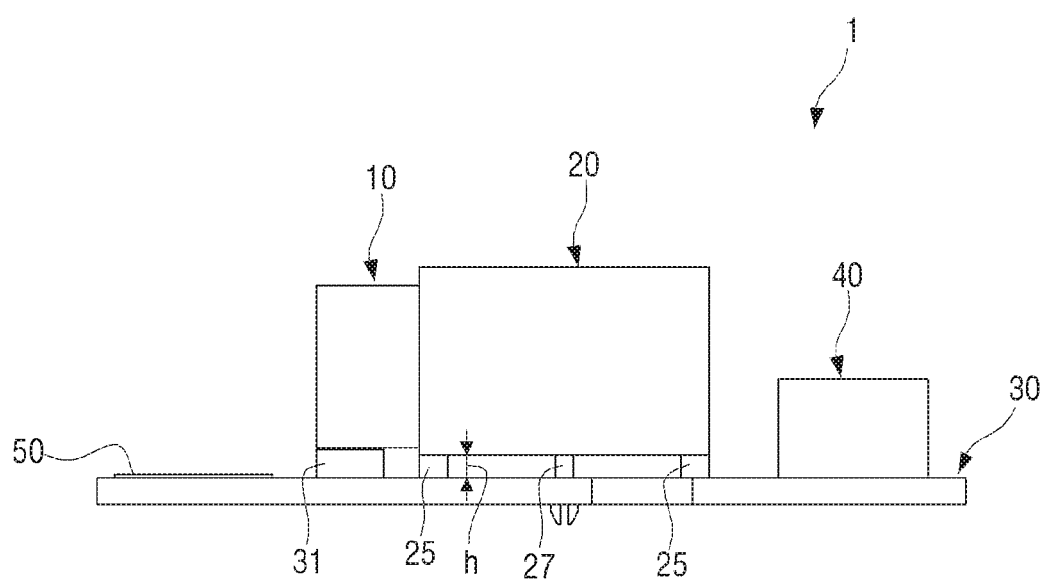
FIG. 3 is a side view illustrating the formaldehyde detecting apparatus of FIG. 1.
Figure 4:
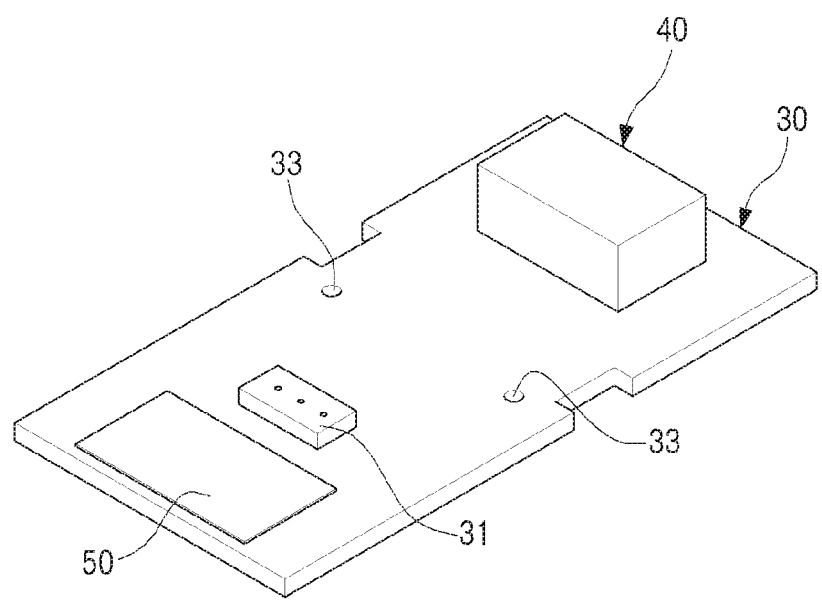
FIG. 4 is a perspective view illustrating a printed circuit board of a formaldehyde detecting apparatus according to an embodiment of the present disclosure.
Figure 5:
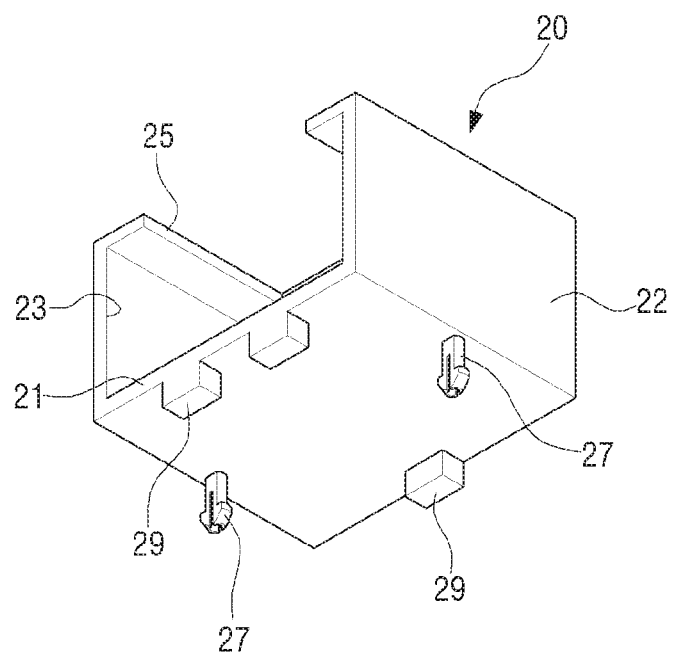
FIG. 5 is a perspective view illustrating an example of a fixing member of a formaldehyde detecting apparatus according to an embodiment of the present disclosure.

FIG. 1 is a perspective view illustrating a formaldehyde detecting apparatus according to an embodiment of the present disclosure. FIG. 2 is a perspective view illustrating a state in which a formaldehyde sensor is separated from the formaldehyde detecting apparatus of FIG. 1, and FIG. 3 is a side view illustrating the formaldehyde detecting apparatus of FIG. 1. FIG. 4 is a perspective view illustrating a printed circuit board of a formaldehyde detecting apparatus according to an embodiment of the present disclosure. FIG. 5 is a perspective view illustrating an example of a fixing member of a formaldehyde detecting apparatus according to an embodiment of the present disclosure.

Referring to FIGS. 1 to 3, a formaldehyde detecting apparatus 1 according to an embodiment of the present disclosure may include a formaldehyde sensor 10, a fixing member 20, and a printed circuit board 30.

The formaldehyde sensor 10 senses formaldehyde in the air and outputs a signal proportional to the concentration of formaldehyde. The formaldehyde sensor 10 may use one of various types such as electrochemical, semiconductor, and resistance types. For example, an electrochemical formaldehyde sensor 10 outputs a current proportional to the concentration of formaldehyde.

The formaldehyde sensor 10 is provided with output terminals 11 at one end portion of the lower surface of the formaldehyde sensor 10. The output terminals 11 output a signal proportional to the concentration of formaldehyde measured by the formaldehyde sensor 10. Since the output terminals 11 are protruded from the lower surface of the formaldehyde sensor 10, when the output terminals 11 are fixed to the printed circuit board 30, the formaldehyde sensor 10 is fixed to the printed circuit board 30. However, in the case in which the formaldehyde sensor 10 is fixed to the printed circuit board 30 by using only the output terminals 11, when external vibration is applied, the formaldehyde sensor 10 vibrates or oscillates based on the output terminals 11 with respect to the printed circuit board 30. Then, the vibration affects the formaldehyde sensor 10, so that the output of the formaldehyde sensor 10 may not maintain the linearity.

In order to prevent the formaldehyde sensor 10 from vibrating based on the output terminals 11 by the external vibration as described above, in the present disclosure, the fixing member 20 is used to fix the formaldehyde sensor 10 to the printed circuit board 30. Then, the formaldehyde sensor 10 is fixed to the printed circuit board 30 by the output terminals 11 and the fixing member 20 so that even when vibration is externally applied, the formaldehyde sensor 10 may be suppressed or prevented from vibrating with respect to the printed circuit board 30.

The fixing member 20 is disposed on the printed circuit board 30 and fixes the formaldehyde sensor 10 to prevent the formaldehyde sensor 10 from vibrating with respect to the printed circuit board 30 by external vibration. The fixing member 20 may include a base portion 21, a fastening portion 27, and a support portion 29.

The base portion 21 supports the formaldehyde sensor 10, and the formaldehyde sensor 10 is fixed to the upper surface of the base portion 21. The base portion 21 may include a housing 22 for fixing the formaldehyde sensor 10. A space 24 is provided inside the housing 22 and an insertion opening 23 is provided on one side of the housing 22 so that the formaldehyde sensor 10 may be inserted into the housing 22. The inner surface of the housing 22 is formed in a shape corresponding to the outer shape of the formaldehyde sensor 10. So, when the formaldehyde sensor 10 is inserted into the housing 22, the formaldehyde sensor 10 may be stably fixed to the housing 22. At this time, the housing 22 may be formed to accommodate about ½ to ⅔ of the formaldehyde sensor 10 in a lengthwise direction. In addition, the upper surface of the housing 22 is provided with an opening 25 through which external air can be in contact with the formaldehyde sensor 10.

The fastening portion 27 fixes the base portion 21 to the printed circuit board 30, and is provided on the lower surface of the base portion 21. In the present embodiment, the fastening portion 27 is formed of a pair of hooks. The pair of hooks 27 is provided on the middle portion of the base portion 21 in the lengthwise direction of the base portion 21 and is spaced apart from each other by a predetermined distance in the widthwise direction of the base portion 21 so that the base portion 21 is stably fixed to the printed circuit board 30. The pair of hooks 27 may be formed to be one-touch coupled to the printed circuit board 30.

The support portion 29 is provided on the lower surface of the base portion 21 so that the base portion 21 may be positioned at a predetermined height on the upper surface of the printed circuit board 30 and may be kept parallel to the printed circuit board 30. The support portion 29 may be formed in a three point support shape so as to stably support the base portion 21. Therefore, the support portion 29 may be formed of three support blocks. In an embodiment illustrated in FIG. 5, two support blocks 29 are provided at the front end of the base portion 21 and one support block 29 is provided at the rear end of the base portion 21.

The height h of the support portion 29 may be determined depending on the length L of the output terminals 11 of the formaldehyde sensor 10 so that the formaldehyde sensor 10 is in closely contact with the printed circuit board 30 by the fixing member 20. In detail, when the output terminals 11 of the formaldehyde sensor 10 are fixed to the printed circuit board 30, the height h of the support portion 29 may be determined by the gap between the lower surface of the formaldehyde sensor 10 and the upper surface of the printed circuit board 30, that is, the height h of the lower surface of the formaldehyde sensor 10. Accordingly, the sum of the thickness of the base portion 21 and the height h of the support portion 29 is determined to be the height of the lower surface of the formaldehyde sensor 10.

In the above description, the fixing member 20 includes the housing 22 provided on the upper surface of the base portion 21. However, the structure of the fixing member 20 is not limited thereto. As long as the fixing member 20 fixes the formaldehyde sensor 10 to the printed circuit board 30 and prevents the formaldehyde sensor 10 from oscillating with respect to the printed circuit board 30, the fixing member 20 may be formed in a variety of structures.

Figure 6:
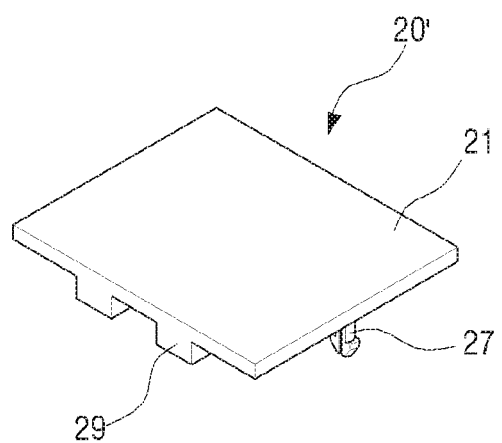
FIG. 6 is a perspective view illustrating another example of a fixing member of a formaldehyde detecting apparatus according to an embodiment of the present disclosure.

For example, the fixing member may be formed as illustrated in FIG. 6.

FIG. 6 is a perspective view illustrating another example of a fixing member of a formaldehyde detecting apparatus according to an embodiment of the present disclosure.

The fixing member 20' illustrated in FIG. 6 is the same as or similar to the fixing member 20 of the above-described embodiment except that the housing 22 (see FIG. 5) is not provided on the upper surface of the base portion 21. In other words, that the fixing member 20' includes a base portion 21, a fastening portion 27, and a support portion 29 is the same as the fixing member 20 as described above.

At this time, the formaldehyde sensor 10 may be fixed to the upper surface of the base portion 21 by various manners. For example, the formaldehyde sensor 10 may be fixed to the base portion 21 as illustrated in FIG. 7.

Figure 7:
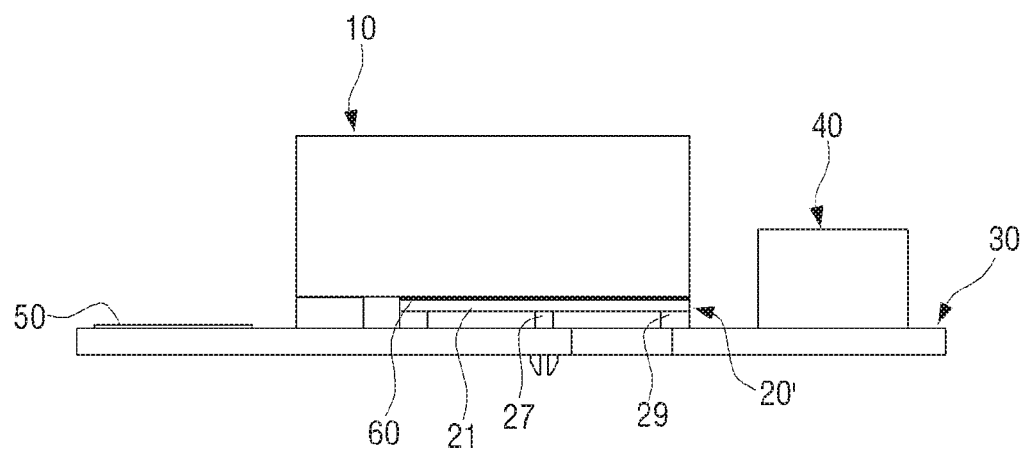
FIG. 7 is a side view illustrating a formaldehyde detecting apparatus according to an embodiment of the present disclosure in which the fixing member of FIG. 6 is disposed.

FIG. 7 is a side view illustrating a formaldehyde detecting apparatus according to an embodiment of the present disclosure in which the fixing member of FIG. 6 is disposed.

Referring to FIG. 7, the formaldehyde sensor 10 may be fixed to the upper surface of the base portion 21 with an adhesive or a double-sided tape 60. In detail, when the adhesive is applied to the upper surface of the base portion 21 or when the double-sided tape is attached to the upper surface of the base portion 21, the base portion 21 of the fixing member 20' may be fixed to the lower surface of the formaldehyde sensor 10.

As another example of the method of fixing the formaldehyde sensor 10 to the base portion 21 of the fixing member 20', although not illustrated, the base portion 21 may be fixed to the lower surface of the formaldehyde sensor 10 by screw fastening. In the case of the screw fastening, the base portion 21 may be provided with at least one screw hole and the lower surface of the formaldehyde sensor 10 may be provided with at least one female screw.

In the above description, the fixing member 20 and 20' are formed to support only a part of the formaldehyde sensor 10. However, as another example, a fixing member 20" may be configured to support the entire lower surface of the formaldehyde sensor 10.

Figure 8:
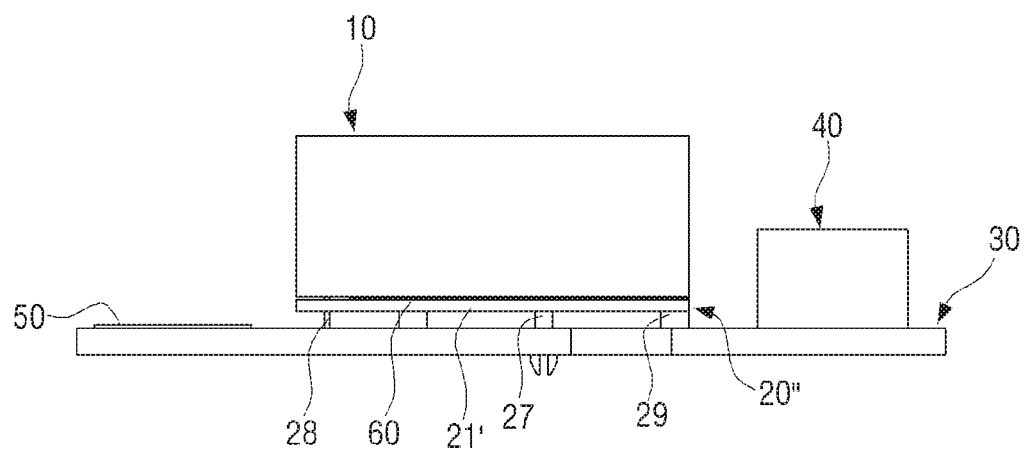
FIG. 8 is a side view illustrating a formaldehyde detecting apparatus according to an embodiment of the present disclosure.

For example, as illustrated in FIG. 8, the base portion 21 of the fixing member 20" may be provided with a terminal adapter 28 to which the output terminals 11 of the formaldehyde sensor 10 are coupled, and the terminal adapter 28 may be coupled to the printed circuit board 30.

FIG. 8 is a side view illustrating a formaldehyde detecting apparatus according to an embodiment of the present disclosure.

The fixing member 20" according to the embodiment illustrated in FIG. 8 has the base portion 21 that supports the entire lower surface of the formaldehyde sensor 10 and is provided with the terminal adapter 28. The base portion 21 of the fixing member 20" is different from the base portion 21 of the fixing members 20 and 20' according to embodiments illustrated in FIGS. 6 and 7. However, the support portion 29 and the fastening portion 27 provided on the lower surface of the base portion 21 of the fixing member 20" are the same as those of the fixing members 20 and 20' according to the embodiments as illustrated in FIGS. 6 and 7.

The fixing member 20" according to the embodiment illustrated in FIG. 8 has a structure in which the formaldehyde sensor 10 is fixed to the base portion 21 by an adhesive or a double-sided tape 60. However, the structure of the base portion 21 is not limited thereto. A housing 22 may be provided on the base portion 21 to fix the formaldehyde sensor 10 like the fixing member 20 as illustrated in FIG. 5.

In the above-description, the formaldehyde sensor 10 is fixed to the printed circuit board 30 by the fixing members 20, 20' and 20" that are formed separately. However, the fixing member 20, 20' and 20" may be formed integrally with the formaldehyde sensor 10.

Figure 9:
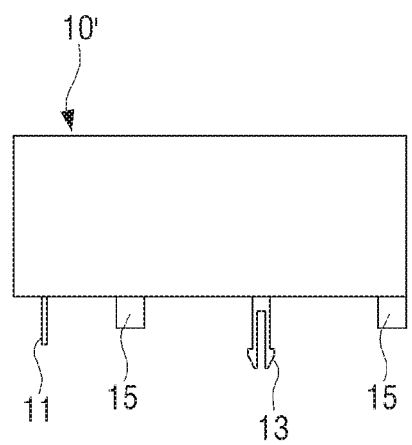
FIG. 9 is a side view illustrating an example of a formaldehyde sensor that can be used in a formaldehyde detecting apparatus according to an embodiment of the present disclosure.

For example, as illustrated in FIG. 9, a support portion 15 and a fastening portion 13 may be provided on the lower surface of a formaldehyde sensor 10' on which the output terminals 11 are provided. When the formaldehyde sensor 10' is disposed on the printed circuit board 30, the formaldehyde sensor 10' is supported by the support portion 15 and is fixed to the printed circuit board 30 by the output terminals 11 and the fastening portion 13. Here, FIG. 9 is a side view illustrating an example of a formaldehyde sensor provided with support portion and fastening portion that can be used in a formaldehyde detecting apparatus according to an embodiment of the present disclosure.

The printed circuit board 30 is provided with the formaldehyde sensor 10 and may allow the formaldehyde detecting apparatus 1 to be fixed to the air treatment apparatus 100. The printed circuit board 30 is formed to fix the fastening portion 27 of the fixing member 20 as described above. For example, when the fastening portion 27 is formed in a pair of hooks, the printed circuit board 30 is provided with a pair of fastening holes 33 into which the pair of hooks 27 is inserted. Accordingly, when the user inserts the pair of hooks 27 of the fixing member 20 into the pair of fastening holes 33 of the printed circuit board 30, the fixing member 20 is fixed to the printed circuit board 30.

Referring to FIG. 4, the printed circuit board 30 may be provided with a fixing portion 31, a circuit portion 50, and a connector 40.

The fixing portion 31 is provided on the upper surface of the printed circuit board 30. The output terminals 11 of the formaldehyde sensor 10 are fixed and electrically connected to the fixing portion 31.

The circuit portion 50 may include a signal processor 51 for processing signals output from the formaldehyde sensor 10 and a power supply for supplying power to the signal processor 51. The circuit portion 50 is not specifically shown, but may be composed of various electronic parts.

The signal processor 51 processes the signal output from the formaldehyde sensor 10. For example, the signal processor 51 is electrically connected to the fixing portion 31 to which the output terminals 11 of the formaldehyde sensor 10 are connected and fixed, and is configured to amplify and filter the signal output from the formaldehyde sensor 10. For example, in the case in which the formaldehyde sensor 10 is an electrochemical sensor, the formaldehyde sensor 10 outputs a fine current through the output terminals 11 when the formaldehyde sensor 10 senses formaldehyde. At this time, the signal processor 51 amplifies the fine current and filters noise.

Figure 10:
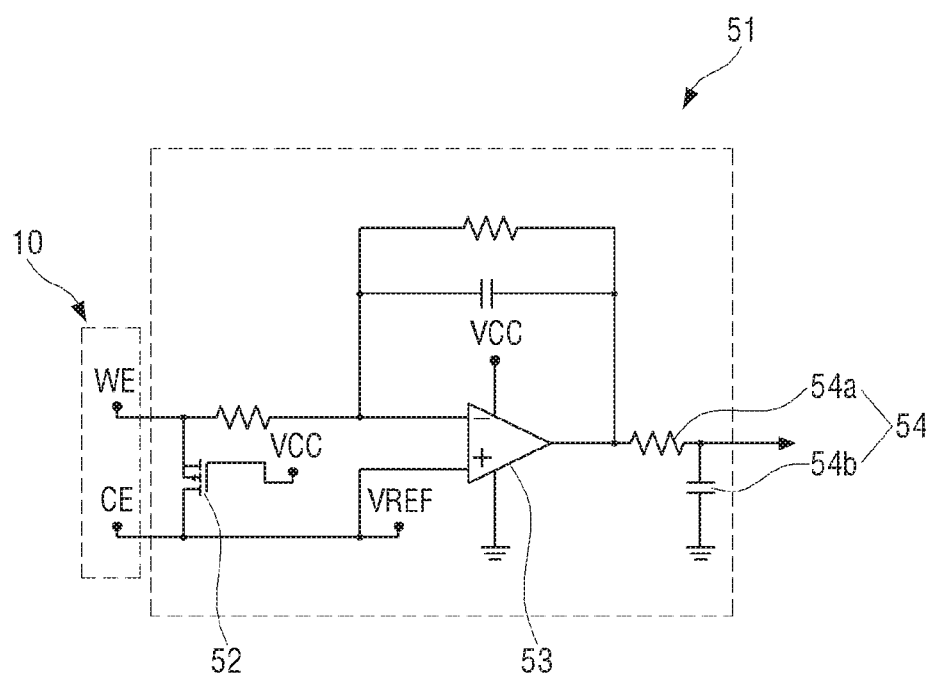
FIG. 10 is a circuit diagram illustrating a signal processor of a formaldehyde detecting apparatus according to an embodiment of the present disclosure.

An example of the signal processor 51 is illustrated in FIG. 10.

FIG. 10 is a circuit diagram illustrating a signal processor of a formaldehyde detecting apparatus according to an embodiment of the present disclosure.

Referring to FIG. 10, the signal processor 51 may include a field effect transistor (FET) 52, an operational amplifier 53, a plurality of resistors, and a plurality of capacitors.

The formaldehyde sensor 10 is connected to the signal processor 51 through two electrodes, that is, a working electrode WE and a corresponding electrode CE. The signal output from the formaldehyde sensor 10 is amplified while passing through the operational amplifier 53. When the amplified signal passing through the operational amplifier 53 passes through a filter 54 connected downstream of the operational amplifier 53, noise is removed. The filter 54 may be composed of a resistor 54a and a capacitor 54b. The amplified signal having passed through the filter 54 may be transmitted to a second signal processor. Since the signal output from the signal processor 51 is an analog signal, the second signal processor may be, for example, an analog-to-digital converter for converting an analog signal into a digital signal.

The power supply 55 is formed to supply a voltage capable of stabilizing the output to the signal processor 51. When the fluctuation of the power VCC supplied to the FET 52 and the operational amplifier 53 of the signal processor 51 is large, the fluctuation of the signal output from the signal processor 51 becomes large. Therefore, even if the formaldehyde sensor 10 outputs a signal proportional to the concentration of formaldehyde, the signal output from the signal processor 51 may not be proportional to the concentration of formaldehyde. In other words, the signal output from the signal processor 51 may not maintain the linearity and become non-linear. In addition, when the fluctuation range of the power supplied to the signal processor 51 is large, the formaldehyde sensor 10 may be affected so that the formaldehyde sensor 10 itself may not output a signal proportional to the concentration of formaldehyde. Therefore, the power supply 55 is formed to supply a power having a small fluctuation range to the signal processor 51 so that the signal output from the signal processor 51 may maintain linearity.

Figure 11:
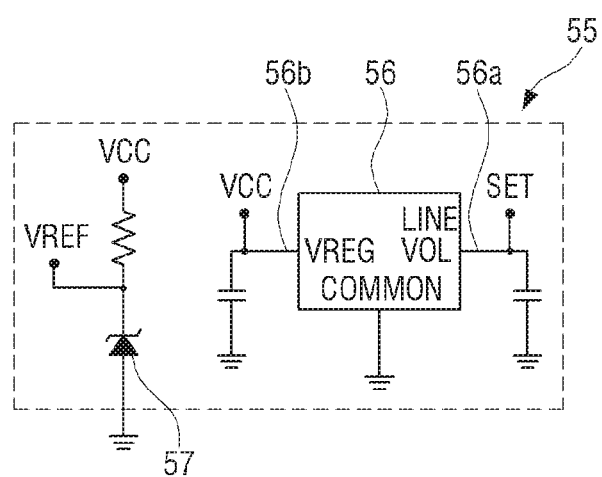
FIG. 11 is a circuit diagram illustrating a power supply of a formaldehyde detecting apparatus according to an embodiment of the present disclosure.

An example of such a power supply 55 is illustrated in FIG. 11.

FIG. 11 is a circuit diagram illustrating a power supply of a formaldehyde detecting apparatus according to an embodiment of the present disclosure.

Referring to FIG. 11, the power supply 55 may include a regulator 56 and a zener diode 57.

The regulator 56 functions to drop the voltage of the input power to a voltage of a desired magnitude and to output a stabilized power by removing noise. Accordingly, the power having passed through the regulator 56 has a small fluctuation range. An external power source SET is connected to an input terminal 56*a* of the regulator 56, and a power VCC of a voltage required for the signal processor 51 is output through an output terminal 56*b* of the regulator 56. Accordingly, since the power stabilized by the regulator 56 is supplied to the signal processor 51, the signal output from the signal processor 51 maintains linearity. Here, the external power source SET refers to a device power source 170 (see FIG. 13) of the air treatment apparatus 100 in which the formaldehyde detecting apparatus 1 is disposed.

For example, when the voltage supplied from the external power source SET is 12V and the voltage required for the signal processor 51 is 5V, the regulator 56 is configured to receive a voltage of 12V and output a voltage of 5V. At this time, the regulator 56 is formed to minimize the voltage deviation by removing noise of the input voltage. For example, the regulator 56 may be configured to reduce the deviation of the output voltage to 0.1% or less. In detail, when the output voltage of the regulator 56 is 5V, the deviation of the output voltage may be ±1 mv or less.

The zener diode 57 is connected to the power VCC output from the regulator 56 and supplies a reference voltage VREF to the operational amplifier 53 of the signal processor 51.

The connector 40 is fixed to the printed circuit board 30 so that the formaldehyde detecting apparatus 1 is supplied with power from the external power source SET and outputs a signal to an external apparatus such as the air treatment apparatus 100.

The formaldehyde detecting apparatus 1 having the above-described structure may be disposed in the air treatment apparatus 100 and detect the concentration of formaldehyde contained in air in the room. Here, the air treatment apparatus 100 may include an air purifier, an air conditioner, a dehumidifier, or the like, which sucks air in the room, performs a predetermined process, and discharges the processed air.

Figure 12:
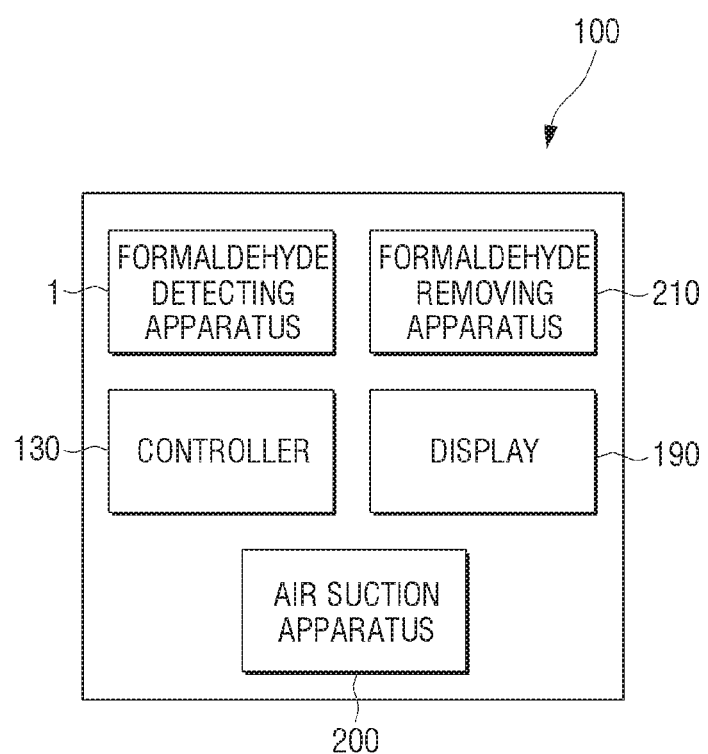
FIG. 12 a functional block diagram illustrating an air treatment apparatus according to an embodiment of the present disclosure.

FIG. 12 a functional block diagram illustrating an air treatment apparatus according to an embodiment of the present disclosure.

Referring to FIG. 12, the air treatment apparatus 100 may include a formaldehyde detecting apparatus 1, a formaldehyde removing apparatus 210, an air suction apparatus 200, a controller 130, and a display 190.

The formaldehyde detecting apparatus 1 detects the concentration of formaldehyde in the air and outputs a signal proportional to the concentration of formaldehyde. Since the structure and operation of the formaldehyde detecting apparatus 1 are described above, detailed descriptions thereof are omitted.

The formaldehyde removing apparatus 210 is provided to remove formaldehyde contained in the sucked air. The formaldehyde removing apparatus 210 may not be disposed in all the air treatment apparatus 100 but be disposed as required. For example, when the air treatment apparatus 100 is an air purifier, the formaldehyde removing apparatus 210 may be provided. However, when the air treatment apparatus 100 is an air conditioner or a dehumidifier, the formaldehyde removing apparatus 210 may not be provided. The formaldehyde removing apparatus according to the prior art may be used as the formaldehyde removing apparatus 210, and thus a detailed description thereof is omitted.

The air suction apparatus 200 sucks outside air into the inside of the air treatment apparatus 100 and discharges the air to the outside of the air treatment apparatus 100. The air suction apparatus 200 may include a motor and a fan. Accordingly, when the motor and the fan of the air suction apparatus 200 are rotated, variation may occur in the air treatment apparatus 100.

When vibration is generated by the operation of the air treatment apparatus 100, in the conventional formaldehyde detecting apparatus, the formaldehyde sensor oscillates or vibrates with respect to the printed circuit board so that the output signal is unstable and nonlinear. However, in the formaldehyde detecting apparatus 1 according to an embodiment of the present disclosure, since the formaldehyde sensor 10 is fixed to the printed circuit board 30 by the fixing member 20, even when vibration occurs due to the operation of the air suction apparatus 200, the output signal may be stabilized and linearity of the output signal may be maintained.

The display 190 is configured to display a status of the air treatment apparatus 100 and various menus through which the user can operate the air treatment apparatus 100. The display 190 is the same as or similar to the display of the air treatment apparatus according to the related art; therefore, a detailed description thereof is omitted.

The controller 130 controls the air treatment apparatus 100 to perform functions of the air treatment apparatus 100. Also, the controller 130 may be configured to receive the signal from the formaldehyde detecting apparatus 1 and inform the user of the concentration of formaldehyde in the air.

Figure 13:
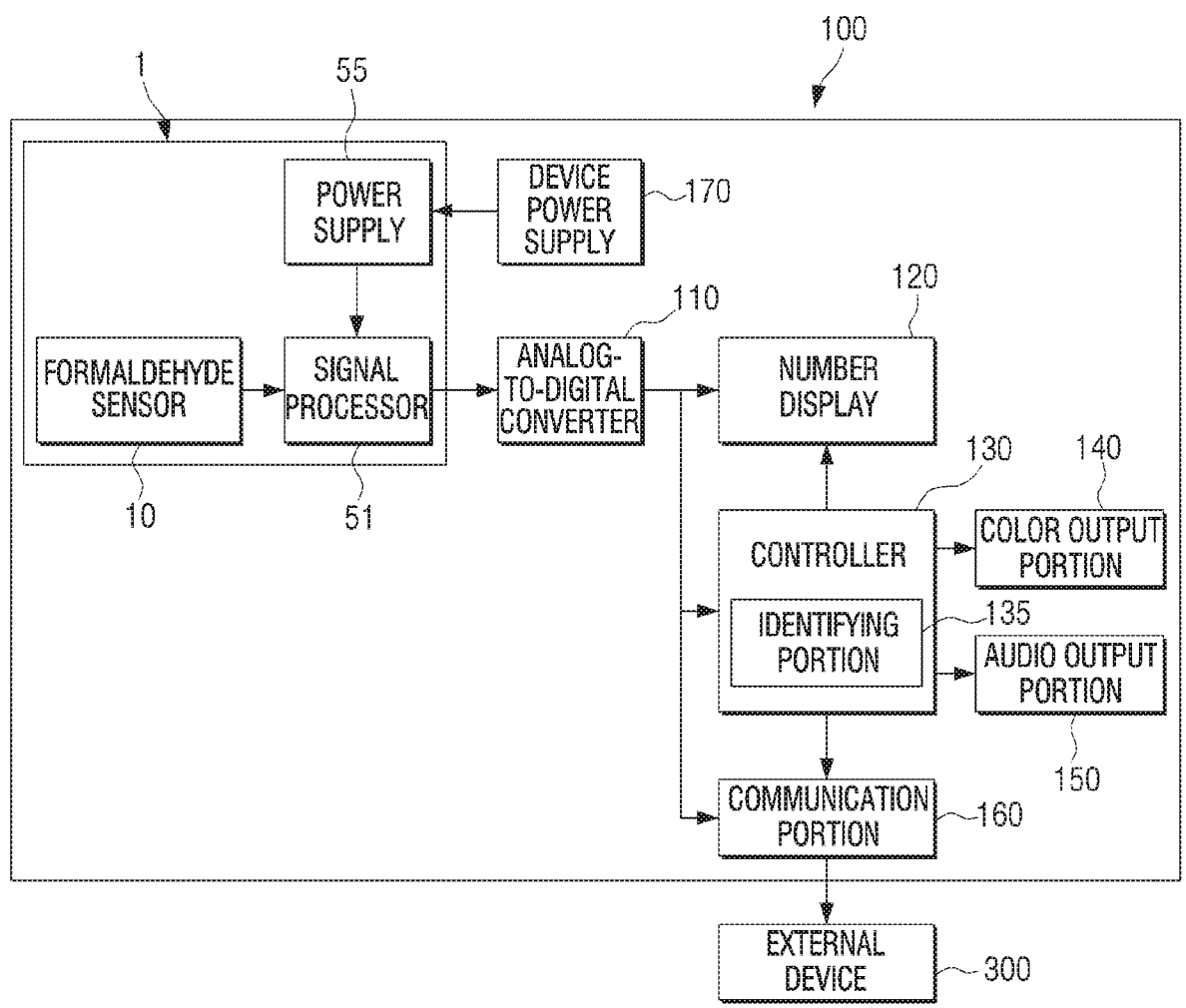
FIG. 13 is a functional block diagram illustrating an example of an air treatment apparatus provided with a formaldehyde detecting apparatus according to an embodiment of the present disclosure.

FIG. 13 is a functional block diagram illustrating an example of an air treatment apparatus provided with a formaldehyde detecting apparatus according to an embodiment of the present disclosure.

Referring to FIG. 13, the air treatment apparatus 100 provided with the formaldehyde detecting apparatus 1 according to an embodiment of the present disclosure may include an analog-to-digital converter 110, a number display 120, and a controller 130.

The analog-to-digital converter 110 converts an analog signal output from the formaldehyde detecting apparatus 1 according to an embodiment of the present disclosure into a digital signal. In the embodiment illustrated in FIG. 13, the analog-to-digital converter 110 is disposed separately from the formaldehyde detecting apparatus 1; however, the analog-to-digital converter 110 may be disposed in the formaldehyde detecting apparatus 1. In this case, the formaldehyde detecting apparatus 1 may output a digital signal.

Figure 14:
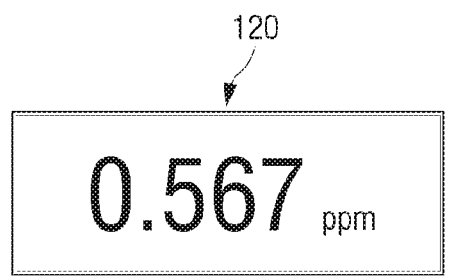
FIG. 14 is a view illustrating a number display used in an air treatment apparatus according to an embodiment of the present disclosure.

The number display 120 displays the digital signal output from the analog-to-digital converter 110, that is, the concentration of formaldehyde in numerals. Accordingly, the user may know the concentration of formaldehyde in the room by viewing the number displayed on the number display 120. The number display 120 may be formed to display a number below the decimal point as illustrated in FIG. 14. As described above, if the number display 120 can display numbers below the decimal point, the concentration of formaldehyde may be expressed in ppm, which is typically used for indicating the concentration of pollutants.

In the air treatment apparatus 100 illustrated in FIG. 13, the number display 120 for outputting the digital signal of the formaldehyde detecting apparatus 1 is separately provided, but the separate number display 120 may not be provided. In this case, the concentration of formaldehyde detected by the formaldehyde detecting apparatus 1 may be output using the display 190 (see FIG. 12) for displaying the state of the air treatment apparatus 100.

In the above description, the digital signal output from the analog-to-digital converter 110 is directly output to the number display 120. Alternatively, the signal output from the analog-to-digital converter 110 may be transmitted to the controller 130.

The controller 130 may output the received signal to the number display 120 or the display 190 to display the concentration of formaldehyde in numerals.

In addition, the controller 130 may include an identifying portion 135 that can identify whether the external air is in a normal state, a state in which ventilation is required, or a dangerous state depending on the concentration of formaldehyde. To this end, the identifying portion 135 may compare the digital signal output from the analog-to-digital converter with a reference value of the formaldehyde concentration. The reference value of the formaldehyde concentration may be stored in a memory of the controller 130.

The controller 130 may display the air condition through the number display 120 or the display 190 by text or inform the user of the air condition by voice or color. To this end, the air treatment apparatus 100 may include at least one of a color output portion 140 and an audio output portion 150.

The color output portion 140 may display the concentration of formaldehyde in color and inform the user of the state of the formaldehyde. For example, the color output portion 140 may be configured of a plurality of color light emitting diodes (LEDs) such as green, blue, and red. When the concentration of formaldehyde in the air measured by the formaldehyde detecting apparatus 1 is in a normal state, the controller 130 may control the color output portion 140 to display green. When the concentration of formaldehyde is in a state in which ventilation is required, the controller 130 may control the color output portion 140 to display blue. Also, when the concentration of formaldehyde is in a dangerous state, the controller 130 may control the color output portion 140 to display red.

The audio output portion 150 may be formed of a speaker and may inform the user of the concentration of formaldehyde in the air by sound. At this time, the controller 130 may control the audio output portion 150 at predetermined time intervals to inform the user about the current concentration of formaldehyde by sound. Alternatively, when the concentration of formaldehyde is changed, for example, when the concentration of formaldehyde increases from the normal state to the state in which ventilation is required, the controller 130 may control the audio output portion 150 to inform the user of the state in which ventilation is required.

The air treatment apparatus 100 may include a communication portion 160 capable of communicating with an external device 300. The communication portion 160 may communicate with the external device 300 by wire or wirelessly. For example, the communication portion 160 may be connected to the external device 300 such as a mobile phone, a smartphone, a tablet computer, or the like via Wi-Fi, and may transmit the concentration of formaldehyde measured by the formaldehyde detecting apparatus 1 to the external device 300. At this time, the controller 130 of the air treatment apparatus 100 may be configured to transmit the concentration of formaldehyde to the external device 300 through the communication portion 160 at predetermined time intervals. Alternatively, the controller 130 may be configured to transmit the concentration of formaldehyde to the external device 300 when receiving a command from the external device 300 through the communication portion 160.

Figure 15:
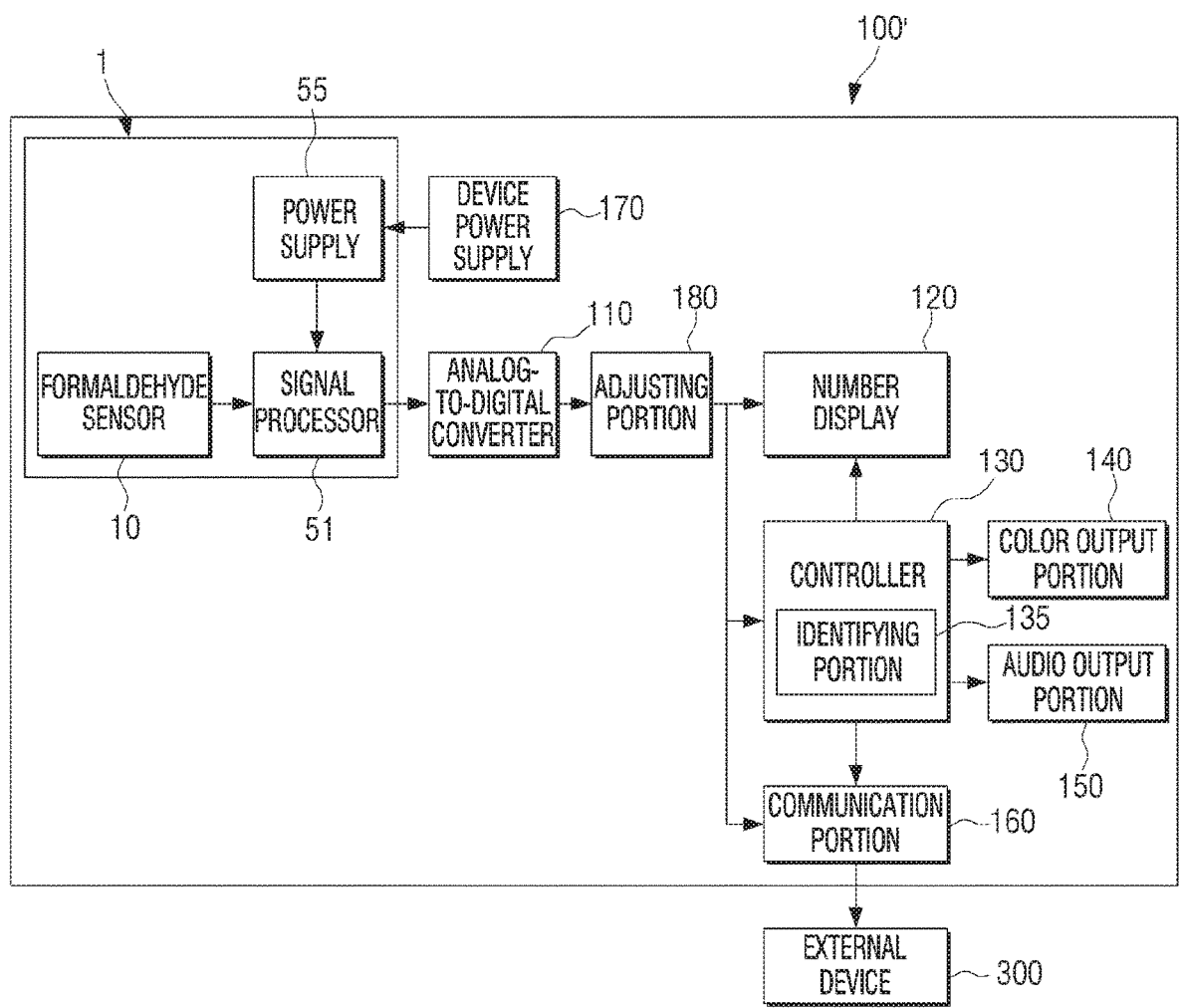
FIG. 15 is a functional block diagram illustrating another example of an air treatment apparatus provided with a formaldehyde detecting apparatus according to an embodiment of the present disclosure.

FIG. 15 is a functional block diagram illustrating another example of an air treatment apparatus provided with a formaldehyde detecting apparatus according to an embodiment of the present disclosure.

Referring to FIG. 15, an air treatment apparatus 100' according to the present embodiment has the same configuration as the air treatment apparatus 100 as illustrated in FIG. 13 except for an adjusting portion 180. Therefore, only the adjusting portion 180 will be described hereinafter.

The signal output from the formaldehyde detecting apparatus 1 provided in the air treatment apparatus 100' may not maintain the linearity due to the structure of the air treatment apparatus 100', the installation position of the formaldehyde detecting apparatus 1 in the air treatment apparatus 100', vibration generated in the air treatment apparatus 100, and the like. The adjusting portion 180 may adjust the signal output from the formaldehyde detecting apparatus 1 to maintain the linearity by reflecting the factors affecting the measured value of the formaldehyde detecting apparatus 1 as described above. For example, the adjusting portion 180 may be implemented as an adjustment algorithm provided in the controller 130.

Figure 16A:
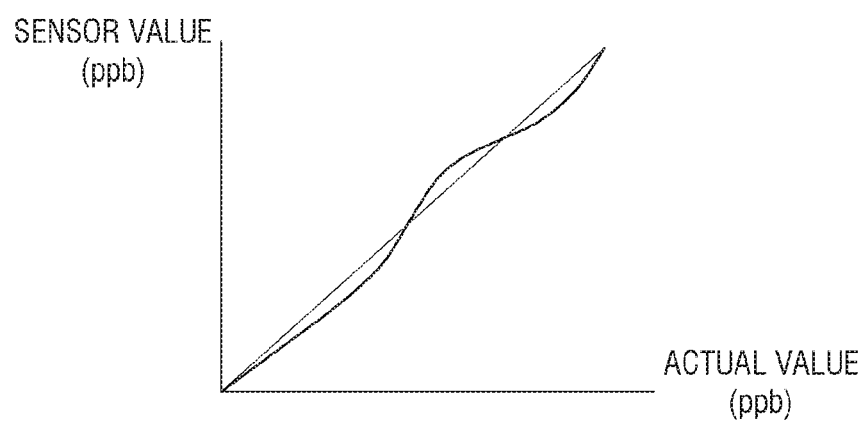
FIG. 16A is a graph illustrating an output signal before adjustment of a formaldehyde detecting apparatus in an air treatment apparatus according to an embodiment of the present disclosure.
Figure 16B:
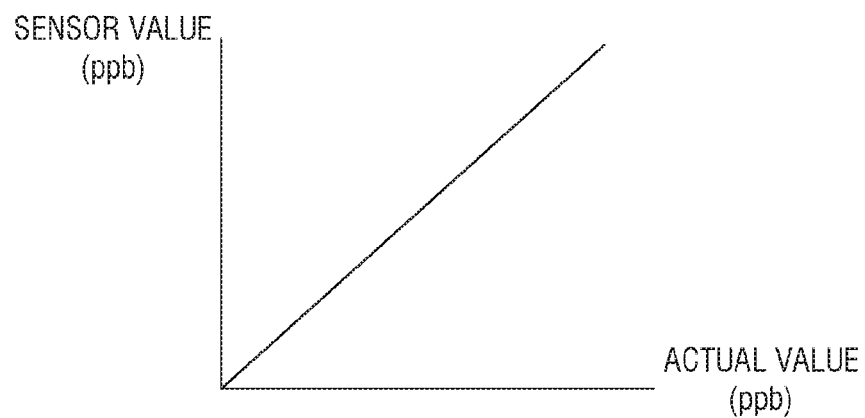
FIG. 16B is a graph illustrating an output signal after adjustment of a formaldehyde detecting apparatus in an air treatment apparatus according to an embodiment of the present disclosure.

FIG. 16A is a graph illustrating an output signal before adjustment of a formaldehyde detecting apparatus in an air treatment apparatus according to an embodiment of the present disclosure, and FIG. 16B is a graph illustrating an output signal after adjustment of a formaldehyde detecting apparatus in an air treatment apparatus according to an embodiment of the present disclosure.

In FIGS. 16A and 16B, both the sensor value and the actual value represent the concentration of formaldehyde. The sensor value represents the concentration of formaldehyde measured by the formaldehyde detecting apparatus 1 provided in the air treatment apparatus 100', and the actual value represents the concentration of formaldehyde measured by the formaldehyde detecting apparatus 1 when there is no influence of the air treatment apparatus 100'.

As illustrated in FIG. 16A, the output signal output from the formaldehyde detecting apparatus 1 provided in the air treatment apparatus 100', that is, the sensor value is not the same as the actual value, but changes depending on the concentration of formaldehyde. In other words, it can be seen that the output signal of the formaldehyde detecting apparatus 1 is non-linear.

However, when the signal output from the formaldehyde detecting apparatus 1 provided in the air treatment apparatus 100' passes through the adjusting portion 180, the signal output from the formaldehyde detecting apparatus 1 is adjusted by the adjustment algorithm of the adjusting portion 180. Accordingly, as illustrated in FIG. 16B, the sensor value coincides with the actual value. In other words, the output signal of the formaldehyde detecting apparatus 1 becomes linear.

The adjustment algorithm of the adjusting portion 180 may be determined depending on the type of the air treatment apparatus 100'. For example, the air purifier and the air conditioner have different configurations, so that the adjustment algorithms for the air purifier and the air conditioner may be different. Further, even in the case of the air treatment apparatus 100' of the same type, the adjustment algorithm may be different when the structure thereof is different.

With the formaldehyde detecting apparatus according to an embodiment of the present disclosure as described above, since the formaldehyde sensor is stably fixed to the printed circuit board by the fixing member and the power supply stably supplies the voltage to the signal processor, a signal proportional to the concentration of formaldehyde may be output. In other words, the output signal of the formaldehyde detecting apparatus according to an embodiment of the present disclosure may be stable and maintain linearity.

In addition, the air treatment apparatus such as an air purifier or an air conditioner including the formaldehyde detecting apparatus according to an embodiment of the present disclosure may accurately identify the current concentration of formaldehyde through the formaldehyde detecting apparatus. Therefore, the air treatment apparatus may accurately inform the user of the concentration of formaldehyde in the air. Accordingly, the user may operate the air treatment apparatus or ventilate the indoor air according to the concentration of formaldehyde informed by the air treatment apparatus.

Further, when the concentration of formaldehyde is above a predetermined value, the air treatment apparatus provided with the formaldehyde detecting apparatus according to an embodiment of the present disclosure may automatically remove formaldehyde by operating the formaldehyde removing apparatus.

While the embodiments of the present disclosure have been described, additional variations and modifications of the embodiments may occur to those skilled in the art once they learn of the basic inventive concepts. Therefore, it is intended that the appended claims shall be construed to include both the above embodiments and all such variations and modifications that fall within the spirit and scope of the inventive concepts.

What is claimed is:

1. A formaldehyde detecting apparatus comprising:
    a printed circuit board including:
        a formaldehyde sensor configured to measure a concentration of formaldehyde in air and including at least one output terminal;
        a signal processor configured to be electrically connected to the at least one output terminal of the formaldehyde sensor through the printed circuit board to process a signal output from the at least one output terminal of the formaldehyde sensor;
        a fixing member fixed to a substrate of the printed circuit board, separate from the at least one output terminal, and configured to receive the formaldehyde sensor to maintain the formaldehyde sensor in a fixed position relative to the signal processor to prevent the formaldehyde sensor from vibrating with respect to the signal processor by external vibration; and
    a power supply configured to supply a voltage to the signal processor,
    wherein the fixing member comprises
        a base portion configured to be fixed to the substrate of the printed circuit board and to receive the formaldehyde sensor to fix the formaldehyde sensor to the substrate of the printed circuit board; and
        a fastening portion extending away from the base portion and configured to fix the base portion to the substrate of the printed circuit board.

2. The formaldehyde detecting apparatus of claim 1, wherein
    the base portion of the fixing member comprises a housing into which the formaldehyde sensor is inserted.

3. The formaldehyde detecting apparatus of claim 1, wherein
    the fastening portion comprises a pair of hooks, and
    wherein the printed circuit board is provided with a pair of fastening holes into which the pair of hooks is inserted.

4. The formaldehyde detecting apparatus of claim 1, wherein
    the fixing member comprises a support portion provided on a lower surface of the base portion, and
    wherein the base portion is located at a predetermined height on the printed circuit board and is kept parallel to the printed circuit board by the support portion.

5. The formaldehyde detecting apparatus of claim 1, wherein
    the formaldehyde sensor is fixed to an upper surface of the base portion with an adhesive or a double-sided tape.

6. The formaldehyde detecting apparatus of claim 1, wherein
    the power supply comprises a regulator that lowers a voltage of a supplied power, removes noise of the supplied power, and output a stabilized voltage.

7. The formaldehyde detecting apparatus of claim 6, wherein
    the voltage supplied to the regulator is 12V, and the voltage output from the regulator is 5V.

8. The formaldehyde detecting apparatus of claim 6, wherein
    deviation of the voltage output from the regulator is 0.1% or less.

9. The formaldehyde detecting apparatus of claim 1, further comprising:
    an analog-to-digital converter electrically connected to the signal processor and configured to convert the signal output from the signal processor into a digital signal.

10. An air treatment apparatus comprising:
    a formaldehyde detecting apparatus provided with a formaldehyde sensor capable of measuring concentration of formaldehyde in air; and
    an air suction apparatus,
    wherein the formaldehyde detecting apparatus comprises,
        a printed circuit board including:
            a formaldehyde sensor configured to measure a concentration of formaldehyde in air and including at least one output terminal;
            a signal processor configured to be electrically connected to the at least one output terminal of the formaldehyde sensor through the printed circuit board to process a signal output from the at least one output terminal of the formaldehyde sensor;
            a fixing member fixed to a substrate of the printed circuit board, separate from the at least one output terminal, and configured to receive the formaldehyde sensor to maintain the formaldehyde sensor in a fixed position relative to the signal processor to prevent the formaldehyde sensor from vibrating with respect to the signal processor by external vibration; and
        a power supply configured to supply a voltage to the signal processor,
        wherein the fixing member comprises
            a base portion configured to be fixed to the substrate of the printed circuit board and to receive the formaldehyde sensor to fix the formaldehyde sensor to the substrate of the printed circuit board; and a fastening portion extending away from the base portion and configured to fix the base portion to the substrate of the printed circuit board.

11. The air treatment apparatus of claim 10, wherein the base portion of the fixing member comprises a housing into which the formaldehyde sensor is inserted.

12. The air treatment apparatus of claim 10, wherein the power supply comprises a regulator that lowers a voltage of a supplied power, removes noise of the supplied power, and output a stabilized voltage.

13. The air treatment apparatus of claim 10, further comprising:
an analog-to-digital converter electrically connected to the signal processor and configured to convert the signal output from the signal processor into a digital signal.

14. The air treatment apparatus of claim 13, further comprising:
a number display configured to display the digital signal output from the analog-to-digital converter by numerals.

15. The air treatment apparatus of claim 14, wherein the number display is configured to display a number below a decimal point.

16. The air treatment apparatus of claim 13, further comprising:
an identifying portion configured to compare the digital signal output from the analog-to-digital converter with a reference value of a formaldehyde concentration; and
an audio output portion configured to output a comparing result of the identifying portion by sound.

17. The air treatment apparatus of claim 13, further comprising:
an adjusting portion configured to adjust the digital signal output from the analog-to-digital converter.

18. The air treatment apparatus of claim 13, further comprising:
a communication portion configured to output the digital signal output from the analog-to-digital converter to an external device.

* * * * *